(12) United States Patent
Gurtner et al.

(10) Patent No.: US 7,470,260 B2
(45) Date of Patent: Dec. 30, 2008

(54) ADMINISTRATION DEVICE COMPRISING A PLUNGER ROD WITH A RETURN LOCK

(75) Inventors: Thomas Gurtner, Koppigen (CH); Fritz Kirchhofer, Sumiswald (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 11/035,031

(22) Filed: Jan. 13, 2005

(65) Prior Publication Data

US 2005/0154352 A1 Jul. 14, 2005

Related U.S. Application Data

(63) Continuation of application No. PCT/CH03/00459, filed on Jul. 8, 2003.

(30) Foreign Application Priority Data

Jul. 16, 2002 (DE) ................................ 102 32 158

(51) Int. Cl.
*A61M 5/00* (2006.01)
*A61M 5/315* (2006.01)

(52) U.S. Cl. ...................... 604/210; 604/224

(58) Field of Classification Search .............. 604/187, 604/140, 156, 214, 136, 129, 208–210, 224, 604/229, 110
See application file for complete search history.

(56) References Cited

U.S. PATENT DOCUMENTS

| 5,545,147 A | * | 8/1996 | Harris ........................ 604/209 |
| 5,611,783 A | | 3/1997 | Mikkelsen |
| 5,643,214 A | | 7/1997 | Marshall et al. |
| 6,221,046 B1 | * | 4/2001 | Burroughs et al. .......... 604/153 |
| 2004/0186431 A1 | * | 9/2004 | Graf et al. .................... 604/124 |

FOREIGN PATENT DOCUMENTS

| DE | 199 00 827 C1 | 1/1999 |
| EP | 0 327 910 B1 | 4/1992 |
| WO | WO 96/07443 | 3/1996 |
| WO | WO 97/36623 | 10/1997 |

* cited by examiner

*Primary Examiner*—Kevin C. Sirmons
*Assistant Examiner*—Andrew M Gilbert
(74) *Attorney, Agent, or Firm*—David E. Bruhn, Esq.; Dorsey & Whitney LLP

(57) ABSTRACT

An administering apparatus including a casing, a reservoir, a piston accommodated in the reservoir such that it can be shifted in an advancing direction, a piston rod which acts on the piston in the advancing direction and forms a first locking mechanism, a second locking mechanism which cannot be moved counter to the advancing direction, a lock element row formed by successively arranged first locking elements, extending in the advancing direction, and formed by one of the locking mechanisms, and a second lock element formed by the other locking mechanism and engaged with the lock element row, wherein it engages with a lock element gap of the lock element row, wherein the second lock element is moved out of engagement by a movement, against an elasticity force, of the piston rod in the advancing direction, but, when engaged, counteracts a movement of the piston rod counter to the advancing direction with a resistance force greater than the elasticity force to prevent the piston rod from moving counter to the advancing direction. In some embodiments, either or both the first and second locking mechanisms form a securing element at one or both ends with respect to the advancing direction, the securing element counteracting a movement of the piston rod counter to the advancing direction with a locking force greater than the resistance force.

12 Claims, 2 Drawing Sheets

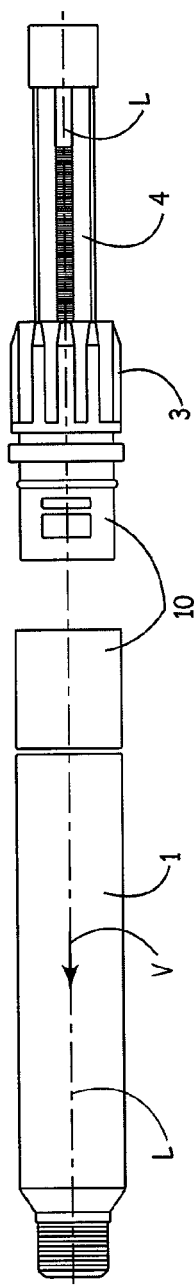
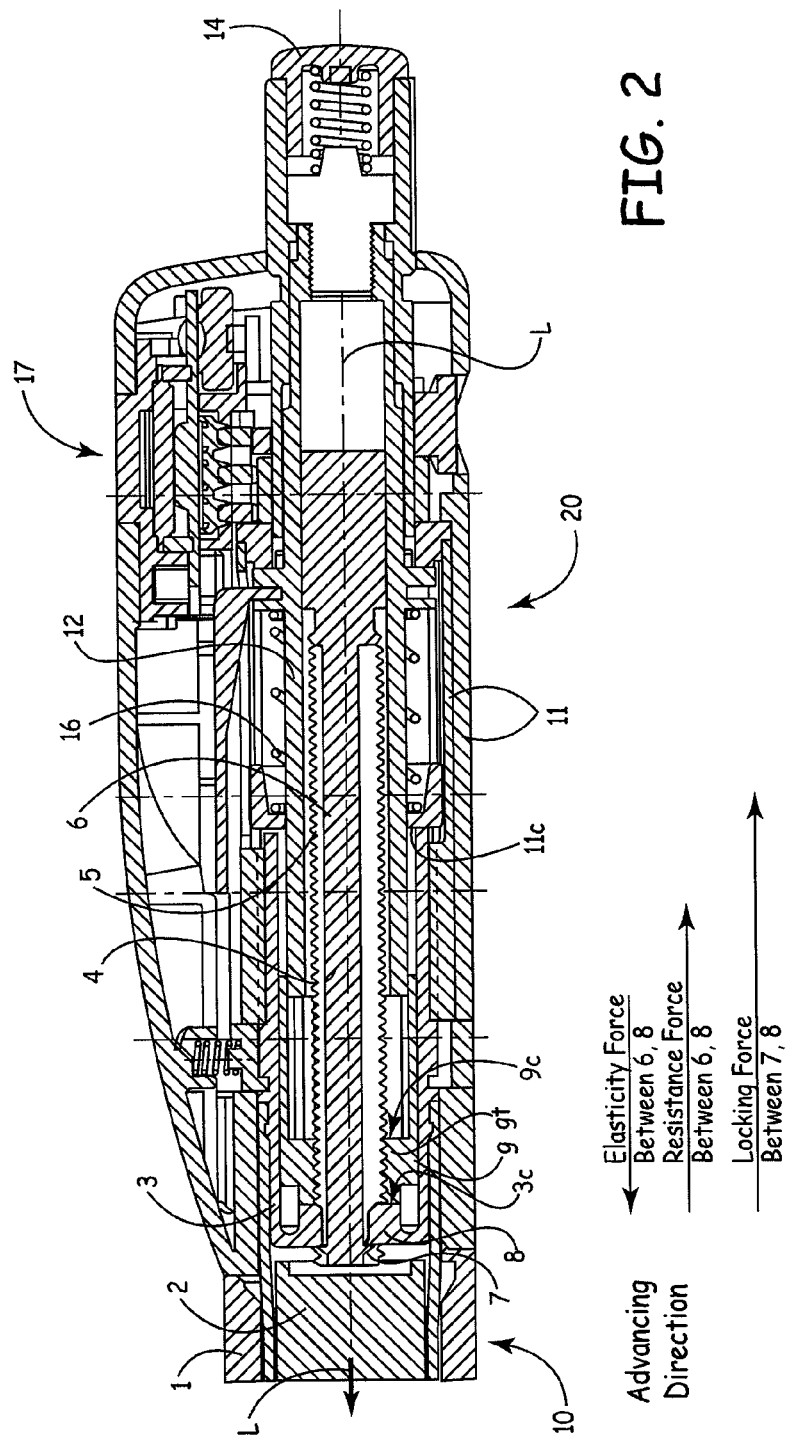

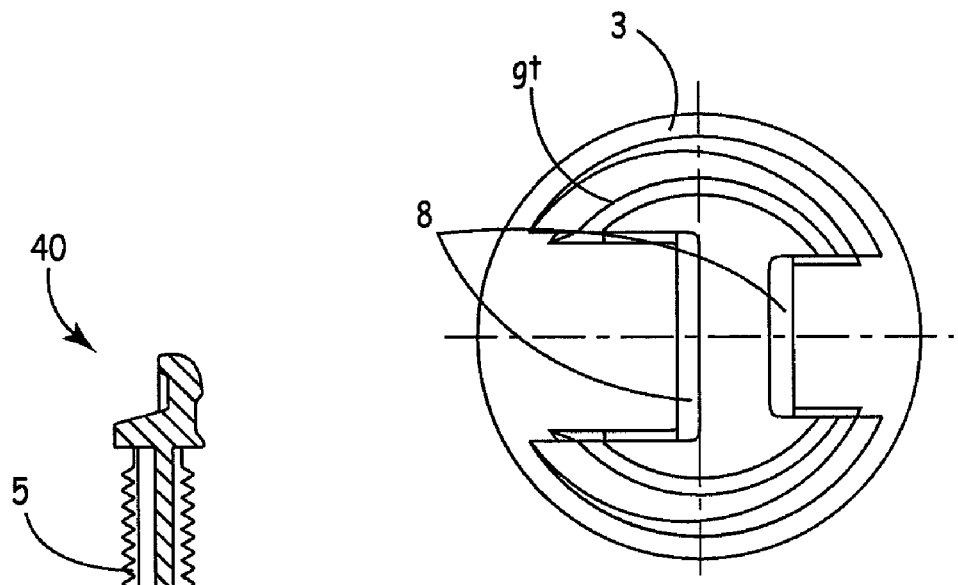
FIG. 5
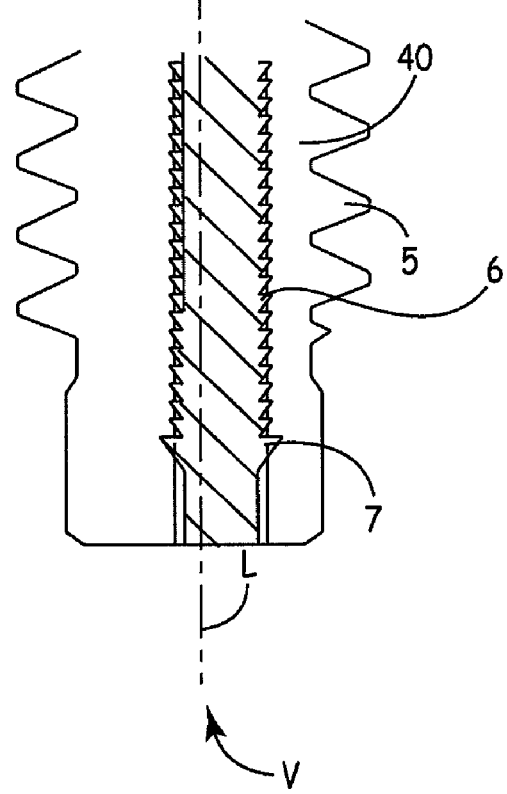
FIG. 3
FIG. 4

ADMINISTRATION DEVICE COMPRISING A PLUNGER ROD WITH A RETURN LOCK

CROSS-REFERENCE TO RELATED APPLICATIONS

This application is a continuation of International Application PCT/CH03/00459, filed on Jul. 8, 2003, which claims priority to German Application No. 102 32 158.2, filed on Jul. 16, 2002, the contents of which is incorporated by reference in its entirety herein.

BACKGROUND

The invention relates to administering apparatus and devices, including injection devices, and methods for administering a fluid product or substance. The main area of application or use is in human medicine. The extended area of application, however, also includes cosmetics and veterinary medicine. In particular, the invention relates to an administering apparatus for self-administering, i.e., a person administering a substance to him or her self, as is, for example, common in diabetes therapy or in administering growth hormones.

Injection apparatus in the form of so-called injection pens, in which the product is delivered from a product reservoir and administered with the aid of a piston, have become known and accepted for self-administering. In some examples, the piston is activated via a piston rod. The piston rod is in engagement with a drive device, in order—by activating the drive device—to move the piston rod and, together with it the piston, in an advancing direction and thus deliver product. Toothed rods are a common type of piston rods. Toothed rods comprise at least one row of teeth extending in the longitudinal direction of the toothed rod. The at least one row of teeth must permit the movement of the piston rod in the advancing direction and can form the engagement with the drive device. A piston rod is usually formed as a toothed rod when a movement of the piston rod counter to the advancing direction is not to be permitted. For this purpose, the row of teeth co-operates with a blocking means, which engages with the row of teeth and thus prevents a returning movement of the piston rod in any axial position which the piston rod can assume during undisrupted operation. Due to the function of the at least one row of teeth as a returning block, administering apparatus comprising piston rods formed as toothed rods are typically apparatus which are completely or partially disposed of once the reservoir has been completely emptied.

In order to ensure that a piston rod formed as a toothed rod is correctly installed, such a piston rod should only be installed in the apparatus by the apparatus manufacturer. Due to the interaction of the returning block, the engagement of the drive device or a dosing mechanism with the piston rod, errors can occur when installing such a piston rod, in particular if the piston rod is installed by a patient or end-user. If the piston rod is installed by the user, there is a danger of the piston rod not being installed correctly with respect to the parts of the administering apparatus to be engaged therewith.

SUMMARY

It is an object of the present invention to reduce the possibility that a user of an injection device or administering apparatus can or will mistakenly or improperly manipulate a component of the device or apparatus. More particularly, it is an object of the present invention to prevent a user from deleteriously manipulating a piston rod of an administering apparatus, even more reliably than with known apparatus and devices.

In one embodiment, the present invention comprises an administering apparatus including a casing, a reservoir, a piston accommodated in the reservoir such that it can be shifted in an advancing direction, a piston rod which acts on the piston in the advancing direction and forms a first locking mechanism, a second locking mechanism which cannot be moved counter to the advancing direction, a lock element row formed by successively arranged first locking elements, extending in the advancing direction, and formed by one of the locking mechanisms, and a second lock element formed by the other locking mechanism and engaged with the lock element row, wherein it engages with a lock element gap of the lock element row, wherein the second lock element is moved out of engagement by a movement, against an elasticity force, of the piston rod in the advancing direction, but, when engaged, counteracts a movement of the piston rod counter to the advancing direction with a resistance force greater than the elasticity force to prevent the piston rod from moving counter to the advancing direction. In some embodiments, either or both the first and second locking mechanisms form a securing element at one or both ends with respect to the advancing direction, the securing element counteracting a movement of the piston rod counter to the advancing direction with a locking force greater than the resistance force.

The invention relates to a device for administering an injectable product, comprising a casing including a reservoir for the product, a piston which can be shifted in the reservoir in an advancing direction, a piston rod which can be moved in the advancing direction and acts on the piston, and a blocking mechanism which serves to prevent the piston rod from moving counter to the advancing direction. The blocking mechanism includes or consists of a first blocking means formed by the piston rod and a second blocking means which cannot be moved counter to the advancing direction relative to the casing, the two blocking means being permanently engaged with each other. The second blocking means can preferably also not be moved in the advancing direction relative to the casing.

The first blocking means is preferably formed integrally with the piston rod. The piston rod can in particular be made from plastic in an original moulding process, for example as an injection moulded part. The second blocking means can be formed separately from the casing and connected appropriately to the casing, but, in some embodiments, is preferably directly formed integrally with a casing section. It, too, can be formed from plastic in an original moulding process suitable for this purpose, in particular injection moulding.

One of the blocking means includes at least one row of first blocking elements arranged successively in the advancing direction. The row of said first blocking elements may be referred to as the blocking element row. The other blocking means includes at least one second blocking element which engages with a single gap or multiple gaps remaining between adjacent first blocking elements in the blocking element row. The blocking element row can in be a row of teeth, preferably a row of serrated teeth, such as is known from known toothed rods. The blocking element row and the second blocking element form a returning block based on the principle of barbs, in order to prevent the piston rod from returning, i.e., moving counter to the advancing direction.

In order to enable movement in the advancing direction, the at least one second blocking element can be moved out of engagement with the blocking element row, against an elasticity force. However, the engagement between the second blocking element and the blocking element row counteracts the returning movement of the piston rod with a resistance force which is significantly greater than the elasticity force which has to be overcome for the advancing movement. In order to generate the elasticity force, in some preferred embodiments, the second blocking element is formed to bend elastically. In principle, however, the second blocking element could also be elastically supported on a separate spring element. The resistance force for preventing the returning movement is based on a positive lock between the blocking element row and the second blocking element.

Since the co-operation between the blocking element row and the second blocking element is intended to prevent the piston rod from returning but permit it to move in the advancing direction, however, limits are set on the resistance force which prevents the returning movement. It is therefore entirely conceivable for a user to retract the piston rod despite the co-operation between the two blocking means, or even to retract it far enough for the blocking means to completely disengage.

In accordance with the present invention, this is prevented by a block securing element formed either by the first blocking means at its front end with respect to the advancing direction or by the second blocking means at its rear end with respect to the advancing direction, said block securing element counteracting a movement of the piston rod counter to the advancing direction with a blocking force which is greater than the resistance force cited. Such a block securing element can also be formed on each of the front end of the first blocking means and the rear end of the second blocking means, although this is not required. The first and/or second blocking means can also comprise a number of block securing elements each.

In some preferred embodiments, the block securing element is formed at one end of the blocking element row. The blocking element row is formed on the piston rod, i.e., the blocking element row forms the first blocking means or at least a part of the first blocking means. If the block securing element is formed on the piston rod, integrally with the piston rod, then it is arranged in front of the blocking element row or second blocking element thus formed, irrespective of whether the first blocking means forms the blocking element row or the second blocking element. If the block securing element is a component of the second blocking means, then it is behind the blocking element row or second blocking element thus formed, irrespective of whether the second blocking means forms the blocking element row or the second blocking element.

In order to generate the blocking force, the block securing element co-operates with a securing counter element in order to prevent the piston rod from detaching from the casing or casing section. In a preferred embodiment, it co-operates either with the blocking element row or with the second blocking element, such that an additional securing counter element just for an engagement is not also needed in order to generate the blocking force, although such an embodiment is also not to be excluded. The block securing element can be formed in the manner of the first blocking elements forming the blocking element row, which facilitates co-operation with the second blocking element. However, it is also fully in accordance with a preferred embodiment if the block securing element is formed in the manner of the second blocking element, in order to be able to co-operate with the blocking element row.

In order to facilitate installing the piston rod, it is preferable if the block securing element permits the movement of the piston rod in the advancing direction. Accordingly, the block securing element should co-operate with the securing counter element essentially like the blocking element row and the second blocking element. An elastic flexibility should obtain between the block securing element and the securing counter element, co-operating in order to generate the blocking force, said elastic flexibility allowing the securing counter element to slide off on the block securing element when the piston rod is moved in the advancing direction. The force which has to be applied in order for the block securing element and the securing counter element to slide off on each other when the piston rod is moved in the advancing direction shall be greater than the elasticity force cited, but on the other hand should be smaller than the resistance force cited.

In some preferred embodiments, the block securing element is arranged with respect to the blocking element row and the second blocking element such that it prevents the blocking element row and the second blocking element from being disengaged. If the block securing element is arranged at one of the two ends of the blocking element row, then it should exhibit the same distance from the nearest adjacent first blocking element as any two nearest adjacent successive first blocking elements, in order to provide that the axial position of the piston rod is always defined. In some preferred embodiments, the block securing element is arranged in the extension of the blocking element row, since in this case, the second blocking element for generating the blocking force can co-operate with the block securing element in the same way with the first blocking elements. If the block securing element is formed in the manner of the second blocking element and the blocking force is generated by the co-operation of the blocking element row, the second blocking element and the block securing element should exhibit a distance from each other in the advancing direction which corresponds to the length of the blocking element row.

In one embodiment, the piston rod comprises a threaded section, in order to form a dosing mechanism or part of a dosing mechanism in a threaded engagement with a threaded nut. In a preferred embodiment, a cavity extending in the advancing direction is formed in the threaded section and one of the blocking means, preferably the blocking element row, is arranged in said cavity. The block securing element is preferably also arranged in the cavity. The blocking means, and the block securing element if it is arranged in the cavity, radially protrude at most to the root of the thread; in some preferred embodiments, they remain radially slightly behind the root of the thread. If the cavity extends beyond the threaded section in or counter to the advancing direction and the blocking means and/or the block securing element in question are arranged in the recess outside the threaded section, then this applies equally, i.e., the blocking means and/or the block securing element in question do not protrude beyond a surface outer area of the piston rod extending the root of the thread. In principle, however, the piston rod can also be formed as a toothed rod without a thread or also with other means for dosing.

The invention can be realized with any type of administering apparatus or injection device which is based on delivering a product by means of a piston and piston rod. It is, however, particularly advantageously used in apparatus in which a used product reservoir is not refilled again. In particular, the invention is advantageous for so-called semi-disposable pens. These are injection apparatus which comprise a reservoir module and a dosing and activating module, wherein they preferably consist only of these two modules. The reservoir module is disposed of once the product contained in its reservoir has been used up, while the dosing and activating module is provided for use with constantly new reservoir modules. The high-quality and therefore expensive parts of the administering apparatus are assembled in the dosing and activating module. Since the reservoir module is not intended for an unlimited number of dosage selection and product delivery procedures, the parts assembled in it can be manufactured inexpensively. Dividing the administering apparatus into a reservoir module which is provided only for a limited number of product deliveries and a dosing and activating module which is not limited with respect to the number of dosing procedures and product deliveries opens up new possibilities for optimising the cost/value ratio of such apparatus.

BRIEF DESCRIPTION OF THE FIGURES

FIG. 1 depicts two parts of a reservoir module of an injection apparatus;

FIG. 2 depicts the injection apparatus in a longitudinal section;

FIG. 3 depicts a piston rod as set forth in the invention, in a longitudinal section;

FIG. 4 depicts a part of the piston rod, in an enlargement; and

FIG. 5 depicts a blocking means for the piston rod, in a front view.

DETAILED DESCRIPTION

The Figures depict an embodiment of a device or components of a device for delivering a selected dosage or amount of a liquid product or substance. The product or substance can be a medicinal substance, for example insulin.

FIG. 1 shows a view of a reservoir part 1 and a mechanism holder 3 which are connected to each other in order to form a reservoir module 10 of an injection apparatus. The reservoir part 1 is substantially a hollow cylinder with a circular cross-section, which comprises at its front end a connecting region for connecting to a needle holder for an injection needle. The reservoir part 1 serves to accommodate a reservoir container which is preferably formed by an ampoule. The reservoir container is filled with an injectable product, for example insulin or a growth hormone. An outlet at the front end of the reservoir container is sealed fluid-tight by a membrane. When the needle holder is fixed to the front end of the reservoir part 1, a rear part of the injection needle pierces the membrane, such that a fluid connection is established between the tip of the injection needle and the reservoir. A rear end of the reservoir container axially opposite the outlet is sealed fluid-tight by a piston which can be shifted towards the outlet of the reservoir container along a longitudinal axis L, in order to force product out of the reservoir container. A piston rod 4 may be seen in FIG. 1 which protrudes into the mechanism holder 3 at a rear end of the mechanism holder 3 facing away from the reservoir part 1 and is mounted by the mechanism holder 3 such that it can be moved towards the reservoir outlet in an advancing direction V which points along the longitudinal axis L.

FIG. 2 shows a rear part of the injection apparatus, in a longitudinal section. The injection apparatus is formed by a reservoir module 10 and a dosing and activating module 20. The rear end of the reservoir module 10 can be seen in FIG. 1. The reservoir container is completely filled with product, such that only the rear part of the piston 2 can still be seen. The piston rod 4 advances the piston 2 in the advancing direction V towards the reservoir outlet, pressing against the piston 2 via its front end. The longitudinal axis L is the translational axis of the piston 2 and the piston rod 4. The piston rod 4 is held by the mechanism holder 3 such that it can be moved in the advancing direction V once a certain resistance has been overcome but cannot be moved counter to the advancing direction V.

The reverse movement of the piston rod 4 counter to the advancing direction V is prevented by a first blocking means formed on the piston rod 4 co-operating with a second blocking means formed by the mechanism holder 3. The first blocking means consists of two rows of teeth 6 which axially extend on two sides of the piston rod 4 facing away from each other. The two rows of teeth 6 consist of serrated teeth arranged successively or serially in a regular axial pitch. The second blocking means consists of two blocking tongues 8 which are formed on the mechanism holder 3, each opposing one of the rows of teeth 6, and each engage with a tooth gap of the facing row of teeth 6 remaining between two adjacent teeth, transverse to the advancing direction V. The serrated teeth of the rows of teeth 6 are sloped in the advancing direction V, in order to permit the translational movement of the piston rod 4 in the advancing direction V. The blocking tongues 8 are each bent outwards against their restoring elasticity force by the advancing serrated teeth. The rear ends of the serrated teeth, however, are formed such that a reverse movement is prevented by the engagement between the blocking tongues 8. In the example embodiment, the serrated teeth of the rows of teeth 6 point at right angles to the longitudinal axis L at their rear ends. In order to be able to retract the piston rod 4 counter to the advancing direction V, against the blocking tongues 8 engaging with the tooth gaps, a resistance force per blocking tongue 8 has to be overcome which is significantly greater than the elasticity force which opposes movement in the advancing direction V. The blocking tongue 8 should be bent into a concave arc with respect to the piston rod 4 and, in such a shape, should furthermore be bent outwards, out of engagement.

A dosage setting member 9 is also accommodated in the mechanism holder 3. The dosage setting member 9 is formed as a threaded nut. Its inner thread 9t is in threaded engagement with a dosing thread 5 of the piston rod 4. The piston rod 4 is linearly guided in the advancing direction V by the mechanism holder 3, secured against rotating with respect to the longitudinal axis L. The dosage setting member 9 is also axially guided by the mechanism holder 3, but can perform a rotational movement about the longitudinal axis L, relative to the mechanism holder 3 and the piston rod 4. The piston rod 4 and the dosage setting member 9 form a spindle drive, in order to select the product dosage to be administered.

The reservoir part 1 and a mechanism holder 3 are connected to each other, secured against rotating and secured against shifting, and together form the reservoir module 10 of the injection apparatus. The reservoir module 10 therefore also includes the piston rod 4 held by means of the blocking tongues 8 and the dosage setting member 9. The reservoir part 1 and a mechanism holder 3 together form a front casing section of the injection apparatus. A rear casing section 11 is connected to this front casing section, secured against rotating and secured against shifting. The rear casing section 11 forms the carrier for a dosing and activating element 12 and, together with the dosing and activating element 12 and a display means 17 and other parts of the injection apparatus, forms the dosing and activating module 20.

Except for the dosage setting member 9 and the piston rod 4, a dosing and activating device of the injection apparatus includes the other components for selecting the product dosage and activating the injection apparatus. In particular, it includes the dosing and activating element 12 and the counting and display means 17 for counting and optically displaying the selected product dosage. Not least, the counting and display means 17 makes the dosing and activating module 20 a high-quality and therefore expensive part of the injection apparatus. While the comparatively inexpensive reservoir module 10 is designed as a disposable module, which is disposed of or reprocessed by a manufacturer once the reservoir has been emptied, the dosing and activating module 20 is intended for repeated use with new reservoir modules 10.

For selecting the product dosage, the dosing and activating element 12 can be rotated about the longitudinal axis L, and is furthermore mounted by the rear casing section 11 such that it can linearly shift along the longitudinal axis L, in and counter to the advancing direction V.

The dosing and activating element 12 is hollow, generally cylindrical and surrounds the piston rod 4 via a front section, via which it also protrudes into the sleeve-shaped dosage setting member 9. A rear section of the dosing and activating element 12 protrudes out beyond a rear end of the casing section 11 and is sealed by a cap 14.

A restoring spring 16 elastically tenses the dosing and activating element 12, counter to the advancing direction, into the rear axial position shown in FIG. 2 which is referred to in the following as the initial position. In the initial position, the dosage can be selected by rotating the dosing and activating element 12 about the longitudinal axis L. Then, also from the initial position, the selected product dosage can be delivered by axially shifting the dosing and activating element 12 in the advancing direction V.

The dosage setting member 9 and the dosing and activating element 12 are axially and linearly guided on each other and connected to each other such that they cannot rotate about the longitudinal axis L. In the event of a rotational movement of the dosing and activating element 12, the dosage setting member—due to the non-rotational connection to the dosing and activating element 12 on the one hand and the threaded engagement with the piston rod 4, which is held by the blocking means 8 and cannot rotate relative to the mechanism holder 3, on the other—is set into a movement composed of a rotational movement component about the longitudinal axis L and a translational movement component along the longitudinal axis L.

Via a rear abutting area, the dosage setting member 9 forms a translational stopper 9c for the dosing and activating element 12. A translational movement of the dosing and activating element 12 relative to the dosage setting member 9 in the advancing direction V is only possible up until the dosing and activating element 12 comes to rest against the stopper 9c. As soon as there is contact on the stopper 9c, the dosing and activating element 12 slaves or drives the dosage setting member 9 in a continuing movement in the advancing direction V, up to a front end position defined by a translational stopper 3c of the mechanism holder 3. The dosage setting member 9 in turn slaves the piston rod 4 due to the threaded engagement.

Proceeding from the initial state of the injection apparatus shown in FIG. 2, the dosage is selected and the product delivered. The dosing and activating element 12 assumes its initial position.

In order to select the dosage to be administered, the dosing and activating element 12 is rotated about the longitudinal axis L. Due to the non-rotational connection, the dosing and activating element 12 slaves the dosage setting member 9 as it rotates. Due to the threaded engagement with the piston rod 4, this dosing rotational movement of the dosage setting member 9 leads to a translational movement of the dosage setting member 9 along the longitudinal axis L, counter to the advancing direction V. The dosage setting member 9 performs the translational movement not only relative to the mechanism holder 3 but also relative to the dosing and activating element 12. This reduces a slight distance between the stopper 9c formed by the dosage setting member 9 and a counter stopper formed by the dosing and activating element 12, in this exemplary embodiment, the free front end of the dosing and activating element 12. In the course of this dosing rotational movement, the axial and angular position of the dosage setting member 9 respectively assumed corresponds to the product dosage which would be delivered if the dosing and activating element 12 were activated. The counting and display means 17 displays this product dosage.

Once the product dosage has been selected, the selected product dosage can be delivered by activating the dosing and activating element 12. The dosing and activating element 12 is activated by pressing it in the advancing direction V. The dosing and activating element 12 thus travels a first part of its path length alone, until it comes to rest against the translational stopper 9c of the dosage setting member 9. In the course of its subsequent axial movement, it then slaves the dosage setting member 9 and the piston rod 4, until the dosage setting member 9 abuts against the translational stopper 3c formed by the mechanism holder 3. At this moment, the delivery stroke is complete. If the dosing and activating element 12 is released, then it slides back to its initial position shown in FIG. 2 due to the elasticity force of the restoring spring 16 which presses counter to the advancing direction V, while the piston rod 4 and the dosage setting member 9 maintain the new axial position which they have just assumed due to the blocking tongues 8 engaging with the rows of teeth 6. Performing the delivery stroke or restoring the piston rod 4 re-sets the counting and display means 17 back to the minimum dosage, in the exemplary embodiment, zeroing it. In the initial position which the dosing and activating element 12 has reached again, the product dosage for the next delivery can be selected, within the limits of the product amount still contained in the reservoir.

FIG. 3 shows a piston rod 40, in a longitudinal section. As far as the features with respect to the dosage selection and product delivery procedures are concerned, the piston rod 40 corresponds to the piston rod 4 installed in the injection apparatus of FIG. 2. The piston rod 40 is also provided with a dosing thread 5 and a first blocking means comprising two rows of teeth 6. The dosing thread 5 and the rows of teeth 6 correspond substantially exactly to those of the piston rod 4 in FIG. 2, such that identical reference numerals are used. One particular feature of the piston rod 40 shown in FIG. 3 is that enlarged serrated teeth 7 are formed at the front end of each of the two rows of teeth 6. The two enlarged serrated teeth 7 each form a block securing element which, engaged with one of the blocking tongues 8 of the injection apparatus of FIG. 2, prevents the piston rod 40 from being completely removed from the mechanism holder 3 counter to the advancing direction V, more reliably than the rows of teeth 6. The rows of teeth 6 and the block securing elements 7 together form the first blocking means.

The block securing elements 7 protrude beyond the serrated teeth of the rows of teeth 6, transversely to the advancing direction V, via their rear ends. The rear ends of the block securing elements 7 also point at right angles to the longitudinal direction L. Since the stopper areas at the rear ends of the block securing elements 7 radially extend longer transversely to the advancing direction, as compared to the serrated teeth of the rows of teeth 6, a returning movement of the piston rod 40 is more reliably prevented when one of the blocking tongues 8 abuts the rear end of the facing block securing element 7 than by the blocking tongues 8 engaging with the gaps of the regular serrated teeth of the rows of teeth 6.

On the other hand, the block securing elements 7 also permit the piston rod 40 to be inserted into the mechanism holder 3 from the rear. When being inserted, the piston rod 40 is slid in the advancing direction V through an opening remaining between the blocking tongues 8 in the mechanism holder 3. When the piston rod 40 is moved in the advancing direction V, the block securing elements 7 slide along on the blocking tongues 8. As the block securing elements 7 slide along, the blocking tongues 8 are elastically bent radially outwardly in the advancing direction V due to the gradually widening block securing elements 7, until the block securing elements 7 have slid over the blocking tongues 8 via their rear ends. At this moment, the blocking tongues 8 snap forwards radially inwardly—due to their elasticity—into tooth gaps remaining between the rear ends of the block securing elements 7 and the nearest adjacent first serrated tooth of the rows of teeth 6 in each case. The two tooth gaps in question are substantially exactly as deep in the radial direction as the regular tooth gaps of the rows of teeth 6. Since, however, the rear ends of the block securing elements 7 forming the stopper areas protrude, transversely to the advancing direction V, beyond the rear stopper areas formed by the serrated teeth of the rows of teeth 6, the blocking effect of the block securing elements 7, based on a positive lock, is reliable. A returning movement of the piston rod 40 counter to the advancing direction V would require the destruction of the second blocking means 8 or—which can be practically ruled out—the destruction of the block securing elements 7. With respect to the engagement between the blocking means 8 and the two rows of teeth, it is far less reliably ensured that the resistance force to be overcome for a returning movement of the piston rod 40 must inevitably lead to the destruction of the second blocking means 8 or/and the rows of teeth 6. With respect to this engagement, there is the danger of the blocking tongues 8 being elastically bent inwardly not only when the piston rod 40 moves in the advancing direction V, but also when it moves counter to the advancing direction V, and then being bent outwardly until they slip off at the rear ends of the serrated teeth of the rows of teeth 6. Due to their essential bending flexibility, the blocking tongues 8 can possibly be bent so far that it is possible for them to slip off in this way. However, when engaging directly behind the two block securing elements 7, the blocking tongues 8 would have to be bent farther, providing they were not destroyed, before they would slip off in this way. A blocking force to be overcome in order to overcome the block securing elements 7 is therefore greater than the resistance force which must be applied in order to overcome the serrated teeth of the rows of teeth 6. The aim is that the piston rod 40 can only be separated from the reservoir module 10 by destroying second blocking means 8 or/and the block securing elements 7.

FIG. 5 shows the second blocking means 8 in a view of its front side. The two blocking tongues 8 can be seen, which protrude inwards from the sleeve body of the mechanism holder 3, transversely to the advancing direction V. Furthermore, the thread 9t of the dosage setting member 9 can also be seen.

The mechanism holder 3 forms the second blocking means 8 integrally. In the exemplary embodiment, the mechanism holder 3 is an injection moulded part. The piston rod 40 is also an injection moulded part and forms its dosing thread 5, the two rows of teeth 6 and the block securing elements 7 integrally.

With respect to the rows of teeth 6 and the block securing elements 7, reference may also be made to the fact that these functional parts of the piston rod 40 are arranged in axial grooves which extend parallel to the longitudinal axis L on mutually opposing sides of the piston rod 40 and interrupt the dosing thread 5. The rows of teeth 6 and the block securing elements 7 remain behind the root of the thread of the dosing thread 5, such that they do not obstruct screwing the piston rod 40 to the dosage setting member 9 and, during operation, do not obstruct the dosing rotational movement of the dosage setting member 9.

In the foregoing description, embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An administering apparatus for administering a fluid product, said administering apparatus comprising:
    a) a casing including a reservoir for the product;
    b) a piston which is accommodated in the reservoir such that it can be shifted in an advancing direction to administer product;
    c) a piston rod which acts on the piston in the advancing direction and forms a first blocking means;
    d) a second blocking means which cannot be moved relative to the casing counter to the advancing direction;
    e) a blocking element row, formed by successively arranged first blocking elements, extending in the advancing direction, and formed by the first blocking means;
    f) a second blocking element formed by the second blocking means and engaged with the blocking element row, wherein it engages with a set of blocking element gaps of the blocking element row, the blocking element gaps arranged between each of the successively arranged first blocking elements; wherein
    g) the second blocking element is moved out of engagement by a movement, against an elasticity force, of the piston rod in the advancing direction, but when engaged counteracts a movement of the piston rod counter to the advancing direction with a resistance force which is greater than the elasticity force to prevent the piston rod from moving counter to the advancing direction; wherein
    h) a block securing element is carried on the first blocking means, said block securing element formed as an end of the blocking element row and protrudes transversely to the advancing direction beyond the successively arranged first blocking elements; and wherein
    i) the piston rod comprises a threaded section and a cavity extending in the advancing direction, in which the first blocking means and block securing element are formed, the block securing element formed in the cavity transversely to the advancing direction and does not protrude beyond a root of the thread of the threaded section.

2. The administering apparatus as set forth in claim 1, wherein the block securing element protrudes beyond the blocking element row transversely to the advancing direction and is more bend-resistant than the first blocking elements.

3. The administering apparatus as set forth in claim 1, wherein the blocking element row is a row of teeth.

4. The administering apparatus as set forth in claim 1, wherein the block securing element generates a blocking force in engagement with the second blocking element.

5. The administering apparatus as set forth in claim 4, wherein the blocking element row is formed by serrated teeth and the block securing element forms a stopper area for the second blocking element, directly at a tapered end of one of the serrated teeth of the blocking element row, wherein the stopper area points counter to the advancing direction.

6. The administering apparatus as set forth in claim 1, wherein the blocking elements of the blocking element row each form a stopper area for the second blocking element, in order through a positive lock to prevent the piston rod from moving counter to the advancing direction, and in that the block securing element also forms a stopper area, in order through a positive lock to prevent the piston rod from moving counter to the advancing direction, and in that the stopper area of the block securing element has at least substantially, preferably exactly, the same distance—measured in the advancing direction—from the stopper area of the nearest adjacent blocking element of the blocking element row as any two stopper areas of nearest adjacent blocking elements of the blocking element row.

7. The administering apparatus as set forth in claim 1, wherein the block securing element is a serrated tooth which widens in a slope up to a serrated tooth end counter to the advancing direction, and at the serrated tooth end forms a stopper area for the second blocking element, pointing counter to the advancing direction.

8. The administering apparatus as set forth in claim 1, wherein the block securing element generates a blocking force in engagement with a securing counter element and permits movement in the advancing direction beyond the securing counter element, in order that the second blocking element can be engaged with the blocking element row.

9. The administering apparatus as set forth in claim 1, further comprising a reservoir module and a dosing and activating module which is detachably connected to the reservoir module, wherein the reservoir module forms a front casing section of the casing which receives the reservoir, the second blocking means and the piston rod which is in engagement with the second blocking means, and wherein the dosing and activating module includes a rear casing section of the casing comprising a dosing and drive means of the administering apparatus.

10. The administering apparatus as set forth in claim 9, said reservoir module comprising:

a) the front casing section of the casing which comprises the reservoir including the piston accommodated in it, the second blocking means and a connecting means for establishing the connection to the dosing and activating module;

b) the dosage setting member which is accommodated by the front casing section such that it can move, in order to perform a dosing movement and a delivery movement which delivers the product;

c) and the piston rod which is connected to the dosage setting member and is in engagement with the second blocking means.

11. An administering apparatus for administering a fluid product, said administering apparatus comprising:

a) a casing including a reservoir for the product;

b) a piston which is accommodated in the reservoir such that it can be shifted in an advancing direction to administer product;

c) a threaded piston rod which acts on the piston in the advancing direction and comprises:

d) axially running inner channels on opposing sides of said piston rod;

e) blocking element rows formed by successively arranged blocking teeth and arranged in each axial running inner channel of said piston rod; and f) a securing element at one end of each of said blocking element rows, wherein the securing element comprises a transverse width larger than a transverse width of the blocking teeth, said securing element formed in the cavity and is positioned behind a root of the thread of said threaded piston rod; and g) a mechanism having a set of blocking engagements, said blocking engagements engaging with said blocking teeth, wherein said blocking engagements are moved out of engagement with said teeth by movement of said piston rod, against an elasticity force, in the advancing direction, and when said blocking engagements are engaged with said teeth, said blocking engagements counteract a movement of the piston rod counter to the advancing direction with a resistance force which is greater than the elasticity force to prevent the piston rod from moving counter to the advancing direction;

h) wherein said blocking engagements engage with said securing element, said securing element counteracting a movement of the piston rod counter to the advancing direction with a blocking force which is greater than the resistance force.

12. The administering apparatus according to claim 11, wherein said securing element is at a proximal end of said piston rod adjacent to said piston.

* * * * *